United States Patent [19]
Deng et al.

[11] Patent Number: 5,589,326
[45] Date of Patent: Dec. 31, 1996

[54] OSMIUM-CONTAINING REDOX MEDIATOR

[75] Inventors: Zhi D. Deng; Gerald F. Sigler, both of Carmel; Nigel A. Surridge, Indianapolis; Christopher D. Wilsey, Carmel; Robert J. McEnroe, Noblesville; Walter W. Jernigan; Rebecca W. Muddiman, both of Indianapolis, all of Ind.

[73] Assignee: Boehringer Mannheim Corporation, Indianapolis, Ind.

[21] Appl. No.: 180,492

[22] Filed: Dec. 30, 1993

[51] Int. Cl.$^6$ .............................. C12Q 1/00; C12Q 1/37; C12Q 1/26
[52] U.S. Cl. .................. 435/4; 435/14; 435/25; 435/817
[58] Field of Search ...................... 435/4, 14, 24, 435/25, 26, 817; 424/5; 430/130

[56] References Cited

U.S. PATENT DOCUMENTS

| | | | |
|---|---|---|---|
| 4,293,310 | 10/1981 | Weber | 424/5 |
| 4,381,978 | 5/1983 | Gratzel et al. | 435/4 |
| 4,526,661 | 7/1985 | Steckhan et al. | 204/73 |
| 4,545,382 | 10/1985 | Higgins et al. | 128/635 |
| 4,711,245 | 12/1987 | Higgins et al. | 128/635 |
| 4,954,414 | 9/1990 | Adair et al. | 435/4 |
| 5,288,636 | 2/1994 | Pollmann et al. | 435/817 |

FOREIGN PATENT DOCUMENTS

| | | | |
|---|---|---|---|
| 0096288B1 | 8/1985 | European Pat. Off. | C25B 3/04 |
| 0127958B1 | 3/1992 | European Pat. Off. | G01N 33/48 |
| 9214741 | 9/1992 | WIPO . | |
| 9214836 | 9/1992 | WIPO . | |

OTHER PUBLICATIONS

Surridge et al; "Jour Phys. Chem", vol. 98(3), pp. 917–923, 1994.
Pishko et al, "Angew Chem Int Ed Engl", vol. 29 No. 1, pp. 82–84, 1990.
Ohara et al, "Anal. Chem", vol. 65, pp. 3512–3517, 1993.
Ohara et al.; "Glucose Electrodes Based On Cross–Linked [Os(bpy)$_2$ Cl]$^{+/2+}$Complexed Poly(1–vinylimidazole) Films"; 1993, pp. 3512–3517, Anal. Chem.
Forster et al.; "Synthesis, Characterization, and Properties of a Series of Osmium–and Ruthenium–Containing Metallopolymers"; 1990; pp. 4372–4377; Macromolecules.
Zakeeruddin et al.; "Towards Mediator Design: Characterization of Tris–(4,4'–Substituted–2,2'–Bipyridine) Complexes of Iron (II), Ruthenium (II) and Osmium (II) as Mediators for Glucose Oxidase of Aspergillus Niger and Other Redox Proteins"; 1992; pp. 253–258; J. Electroanal. Chem.
Collin et al.; "Anodic Electropolymerization of Films of Polypyrrole Functionalized with Metal Terpyridyl Redox Centres"; 1990; pp. 75–87; J. Electroanal. Chem.
Garguilo et al.; "Amperometric Sensors for Peroxide, Choline, and Acetylcholine Based on Electron Transfer between Horseradish Peroxidase and a Redox Polymer"; 1993; pp. 523–528; Anal. Chem.
Pishko et al.; "Direct Electrical Communication Between Graphite Electrodes and Surface Adsorbed Glucose Oxidase/Redox Polymer Complexes"; 1990; pp. 82–84; Angew. Chem. Int. Ed. Engl.
Geraty et al., "Characterization, Electrochemical and Photochemical Properties of Ruthenium Containing Poly–N–vinylimidazole Coatings", 1984, pp. 389–393, J. Electroanal. Chem.

*Primary Examiner*—Michael G. Wityshyn
*Assistant Examiner*—Louise N. Leary
*Attorney, Agent, or Firm*—D. Michael Young; Max J. Kenemore; Marilyn L. Amick

[57] ABSTRACT

A new group of Os(II) and Os(III) compounds useful as redox mediators in electrochemical biosensors. These compounds have 1) low oxidation potential, 2) fast reaction kinetics between the electroactive center of an enzyme and the compound, 3) slow oxidation of osmium by oxygen, and 4) excellent solubility in aqueous medium. These mediators are particularly useful as a component of a reagent used in an electrochemical biosensor, wherein the biosensor is useful for measuring analytes from a biological fluid, such as blood.

11 Claims, 7 Drawing Sheets

E vs. Ag/AgCl (volts)

OSMIUM-CONTAINING REDOX MEDIATOR

FIELD OF INVENTION

This invention relates to redox mediators and more specifically to redox mediators useful in electrochemical biosensors.

BACKGROUND OF THE INVENTION

Redox mediators (electron transfer agents) have been employed extensively in electrochemical biosensors used for diagnostic testing of analytes such as glucose, cholesterol, fructose, galactose, nitrate, sulfide, bilirubin and various amino acids. The function of the redox mediator is to shuttle electrons efficiently from the enzymes specific for the analyte (for example, glucose oxidase when glucose is the analyte being measured) to the biosensor's electrode surface. It is a critical component for the successful operation of an electrochemical biosensor. However, many redox mediators used in electrochemical biosensors display notable interference from electroactive species present in samples being measured. Interferents include ascorbic acid, uric acid, acetaminophen and bilirubin. Minimizing interference from these electroactive species presents a formidable challenge in electrochemical biosensor research.

SUMMARY OF THE INVENTION

The invention is a new group of compounds having the following formula:

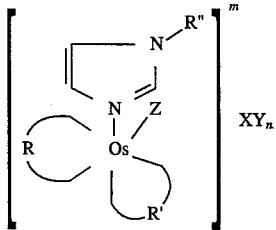

wherein

R and R' are the same or different and are 2,2'-bipyridyl, 4,4'-disubstituted-2,2'-bipyridyl, 5,5'-disubstituted-2,2'-bipyridyl, 1,10-phenanthrolinyl, 4,7-disubstituted-1,10-phenanthrolinyl, or 5,6-disubstituted-1,10-phenanthrolinyl, wherein the disubstitution is a methyl, ethyl, or phenyl group, R and R' are coordinated to Os at their nitrogen atoms, R" is hydrogen, methyl or ethyl, Z is chloro or bromo, M is +1 or +2, X is an anion and is chloride, bromide, iodide, flouride, tetrafluoroborate, perchlorate, nitrate, sulfate, carbonate, or sulfite, Y is an anion and is chloride, bromide, iodide, flouride, tetrafluoroborate, perchlorate, or nitrate, and N is 1 or zero, but when X is sulfate, carbonate, or sulfite, N is zero, and when M is 1, N is zero and X is not sulfate, carbonate or sulfite, wherein the aqueous solubility of the compound is greater than about 1 millimolar (mM).

These compounds are useful as redox mediators in electrochemical biosensors. (Redox mediators are also referred to as electron transfer agents or electron transfer mediators.) The present inventive compounds possess the important and unique combination of 1) low oxidation potential (preferably an $E_{1/2}$ from about 0 millivolts (mV) to about 150 mV vs. silver/silver chloride (Ag/AgCl) reference electrode), 2) fast reaction kinetics between the electroactive center of an enzyme and the compound, 3) slow oxidation of osmium by oxygen, and 4) excellent solubility in aqueous medium, such as whole blood or blood serum. Compounds with less than all four of these characteristics provide poorer performance in an electrochemical biosensor designed to detect or measure blood analytes, such as glucose, and are outside the scope of the present invention.

The low oxidation potential of the present inventive compounds enables an electrochemical biosensor to operate at potentials where interferences from electroactive species, such as bilirubin, acetaminophen, ascorbic acid and uric acid, are low.

Fast reaction kinetics between the electroactive center of an enzyme and the compound enables the compound to compete more efficiently with interfering species in capturing electrons from the enzyme's redox center. For example, when glucose is being measured from a blood sample and glucose oxidase (GOD) is utilized as the enzyme to facilitate the oxidation of glucose, oxygen in the blood sample can compete with a redox mediator for capturing electrons from GOD's redox center (the flavin adenine dinucleotide (FAD) portion of GOD). The compounds of the present invention have sufficiently fast reaction kinetics between the compound and the FAD portion of GOD that competition from oxygen is reduced and in some cases is insignificant.

Oxidation of the redox mediator by molecular oxygen (present in physiological samples) in an electrochemical assay results in assay errors. This error is insignificant with the present inventive compounds because the oxidation of these compounds by oxygen is very slow.

It is important for the redox mediator used in an electrochemical biosensor to be quite soluble in aqueous medium because many important analytical samples, such as whole blood or blood serum, are aqueous based. The present inventive compounds have excellent solubility in aqueous medium.

DESCRIPTION OF THE INVENTION

Figure 1:
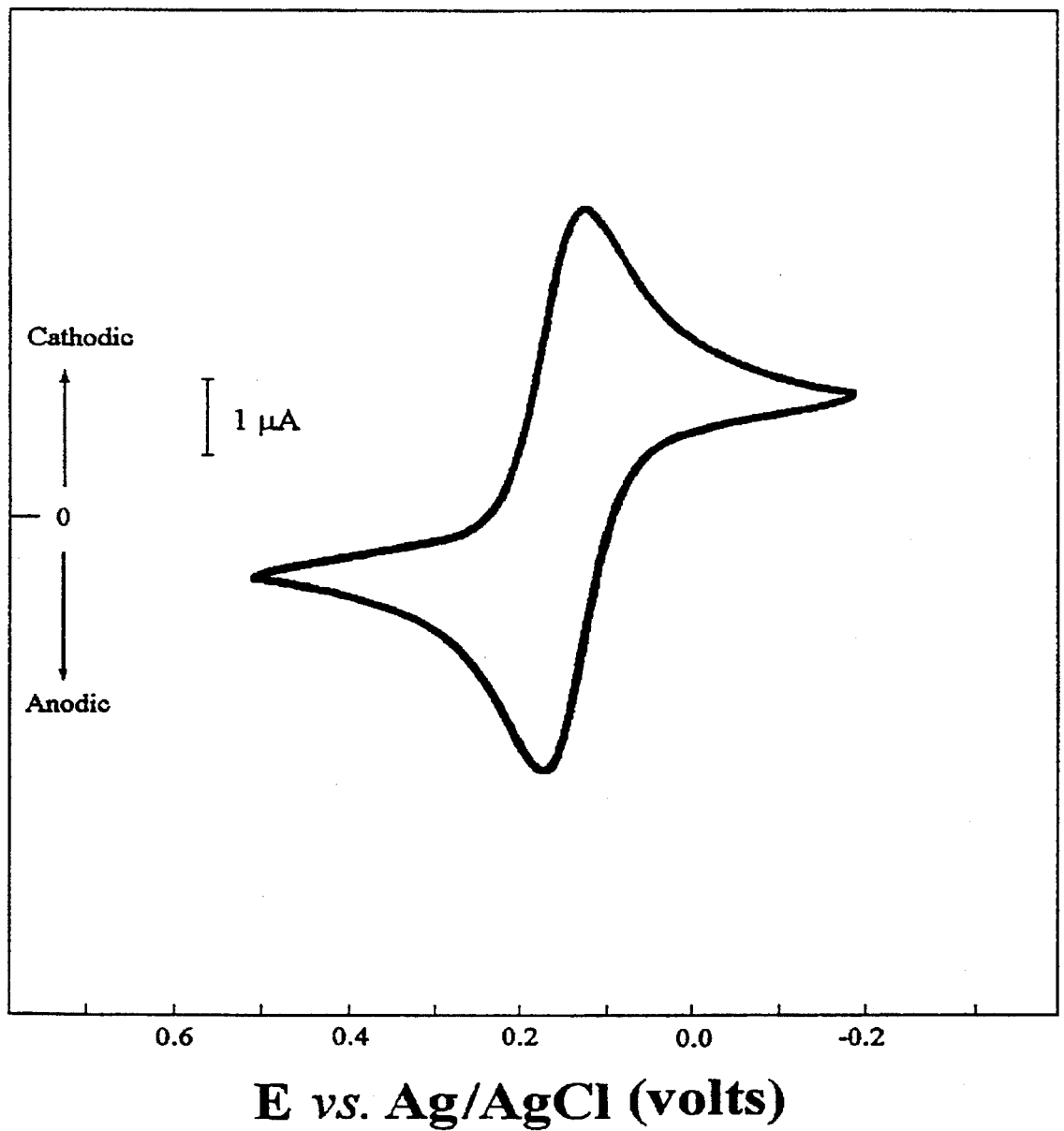
FIG. 1 is a cyclic voltammagram of [Os(III)(bpy)$_2$imCl]Cl$_2$, wherein im is imidazolyl.

The present invention is an important new class of redox mediators, which are useful in electrochemical biosensors. The compounds have the following chemical formula:

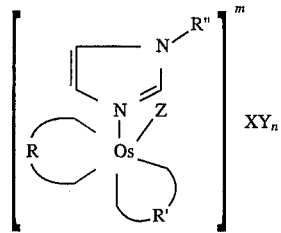

wherein

R and R' are the same or different and are 2,2'-bipyridyl, 4,4'-disubstituted-2,2'-bipyridyl, 5,5'-disubstituted-2,2'-bipyridyl, 1,10-phenanthrolinyl, 4,7-disubstituted-1,10-phenanthrolinyl, or 5,6-disubstituted-1,10-phenanthrolinyl, wherein the disubstitution is a methyl, ethyl, or phenyl group, R and R' are coordinated to Os at their nitrogen atoms, R" is hydrogen, methyl or ethyl, Z is chloro or bromo, M is +1 or +2, X is an anion and is chloride, bromide, iodide, flouride, tetrafluoroborate, perchlorate, nitrate, sulfate, carbonate, or sulfite, Y is an anion and is chloride, bromide, iodide, flouride, tetrafluoroborate, perchlorate, or nitrate, and n is 1 or zero, but when X is sulfate, carbonate, or sulfite, N is zero, and when M is 1, n is zero and X is not sulfate, carbonate or sulfite, wherein the aqueous solubility of the compound is greater than about 1 millimolar (mM).

These compounds possess the following advantageous combination of characteristics: 1) a low oxidation potential, 2) fast reaction kinetics between the electroactive center of an enzyme and the compound (a redox mediator), 3) slow oxidation of osmium by oxygen, and 4) excellent solubility in aqueous medium.

The compounds of the present invention are useful as redox mediators in co-pending and commonly owned U.S. patent application Ser. No. 07/627,667, Pollmann et al. filed Dec. 14, 1990, now U.S. Pat. No. 5,288,636 the disclosure of which is hereby incorporated by reference. The present inventive compounds are also useful as redox mediators in the inventions described in Nankai et al., U.S. Pat. No. 5,120,420, issued Jun. 9, 1992, Nankai et al., U.S. Pat. No. 4,897,173, issued Jan. 30, 1990, Shanks et al., U.S. Pat. No. 5,141,868, issued Aug. 25, 1992, and Kawaguri et al., U.S. Pat. No. 5,171,689, issued Dec. 15, 1992, the disclosures of which are hereby incorporated by reference.

SYNTHESIS OF COMPOUNDS

The compounds of the present invention may be made by the following general scheme, illustrated in flow chart form:

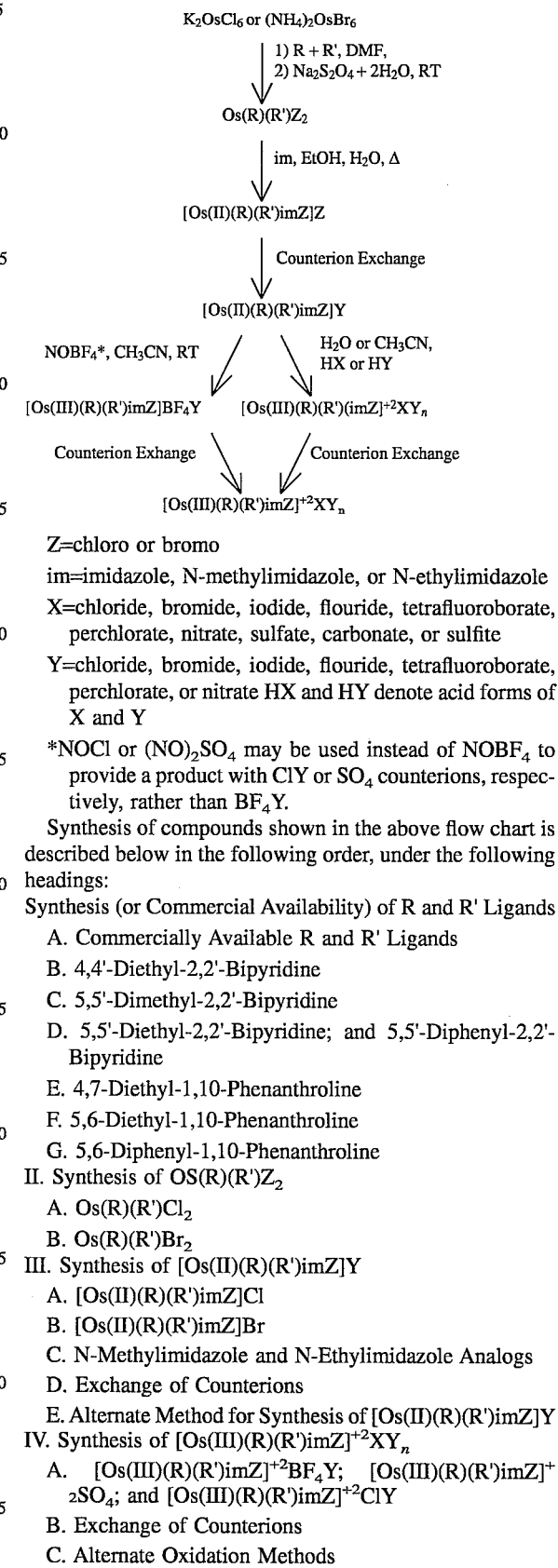

Z=chloro or bromo im=imidazole, N-methylimidazole, or N-ethylimidazole

X=chloride, bromide, iodide, flouride, tetrafluoroborate, perchlorate, nitrate, sulfate, carbonate, or sulfite Y=chloride, bromide, iodide, flouride, tetrafluoroborate, perchlorate, or nitrate HX and HY denote acid forms of X and Y

*NOCl or $(NO)_2SO_4$ may be used instead of $NOBF_4$ to provide a product with ClY or $SO_4$ counterions, respectively, rather than $BF_4Y$.

Synthesis of compounds shown in the above flow chart is described below in the following order, under the following headings:

Synthesis (or Commercial Availability) of R and R' Ligands

A. Commercially Available R and R' Ligands

B. 4,4'-Diethyl-2,2'-Bipyridine

C. 5,5'-Dimethyl-2,2'-Bipyridine

D. 5,5'-Diethyl-2,2'-Bipyridine; and 5,5'-Diphenyl-2,2'-Bipyridine

E. 4,7-Diethyl-1,10-Phenanthroline

F. 5,6-Diethyl-1,10-Phenanthroline

G. 5,6-Diphenyl-1,10-Phenanthroline

II. Synthesis of $OS(R)(R')Z_2$

A. $Os(R)(R')Cl_2$

B. $Os(R)(R')Br_2$

III. Synthesis of $[Os(II)(R)(R')imZ]Y$

A. $[Os(II)(R)(R')imZ]Cl$

B. $[Os(II)(R)(R')imZ]Br$

C. N-Methylimidazole and N-Ethylimidazole Analogs

D. Exchange of Counterions

E. Alternate Method for Synthesis of $[Os(II)(R)(R')imZ]Y$

IV. Synthesis of $[Os(III)(R)(R')imZ]^{+2}XY_n$

A. $[Os(III)(R)(R')imZ]^{+2}BF_4Y$; $[Os(III)(R)(R')imZ]^+_2SO_4$; and $[Os(III)(R)(R')imZ]^{+2}ClY$ B. Exchange of Counterions C. Alternate Oxidation Methods

I. Synthesis (or Commercial Availability) of R and R' Ligands

A. Commercially available R and R' Ligands

The following R and R' compounds are commercially available from Aldrich Chemical Co.: 2,2'-bipyridine; 4,4'-dimethyl-2,2'-bipyridine; 4,4'-diphenyl-2,2'-bipyridine; 1,10-phenanthroline; 4,7-dimethyl-1,10-phenanthroline; 4,7-diphenyl-1,10-phenanthroline; and 5,6-dimethyl-1,10-phenanthroline.

Other R and R' compounds may be synthesized as shown below.

B. 4,4'-Diethyl-2,2'-Bipyridine 4,4'-Diethyl-2,2'-bipyridine may be synthesized according to the procedure described in Rosevear et al., Journal of Heterocyclic Chemistry, vol. 8, pages 483–485 (1971), the disclosure of which is hereby incorporated by reference.

1 gram (g) of 5% or 10% palladium-on-carbon catalyst and 25 milliliters (ml) 4-ethylpyridine are heated for 3 days under reflux while being stirred. (Alternatively, 5% platinum-on-carbon or 5% rhodium-on-carbon may be used as the catalyst.) The reaction mixture is treated with boiling benzene, filtered, and distilled to give benzene, 4-ethylpyridine, and 4,4'-diethyl-2,2'-bipyridine.

C. 5,5'-Dimethyl-2,2'-Bipyridine 5,5'-Dimethyl-2,2'-bipyridine may be synthesized according to the procedure described in Case, J. Am. Chem. Soc., vol. 68, pages 2574–2577 (1946), the disclosure of which is hereby incorporated by reference.

First, 2-bromo-5-methylpyridine is prepared as follows:

A mixture of 55 g of 5-methyl-2-pyridone and 180 g phosphorus tribromide is heated at 180°–190° C. for 3 hours. After cooling, the contents of the flask are decomposed with ice water, made alkaline with sodium hydroxide, and extracted with ether. After removal of the ether, the residue is vacuum-distilled. Redistillation may be necessary.

2-Bromo-5-methylpyridine may also be produced by the method of Craig (Craig, J. Am. Chem. Soc., vol. 56, page 232 (1934), the disclosure of which is hereby incorporated by reference) as follows:

To a solution of 12 g of 2-amino-5-methylpyridine in 70 milliliters (ml) of 47% hydrobromic acid is added 17 ml of bromine. A solution of 21 g of sodium nitrite in 30 ml of water is then added gradually, keeping the temperature below 5° C. until near the end of the reaction when it rises spontaneously to about 10° C. A solution of 45 g of sodium hydroxide in 115 ml of water is then added, keeping the temperature below 25° C. The resulting oil is extracted with ether and distilled under vacuum. Product may be redistilled at atmospheric pressure.

5,5'-Dimethyl-2,2'-bipyridine may be prepared from 2-bromo-5-methylpyridine as follows:

A mixture of 18.5 g of 2-bromo-5-methylpyridine and 29 g of copper powder is heated to 220° C., and the temperature gradually is raised to 240° C. during the course of three-fourths of an hour. After cooling, the reaction mixture is extracted with dilute hydrochloric acid, made alkaline with a sodium hydroxide-ammonium hydroxide mixture, and extracted with ether. Ether may be removed by rotary evaporation.

D. 5,5'-Diethyl-2,2'-Bipyridine; and 5,5'-Diphenyl-2,2'-Bipyridine

Similarly, 5,5'-diethyl-2,2'-bipyridine; and 5,5'-diphenyl-2,2'-bipyridine may be prepared by the same procedure as described above for 5,5'-dimethyl-2,2'-bipyridine by substituting the appropriate pyridone or pyridine compound in the above procedure (for example, substitute 5-ethyl-2-pyridone or 2-amino-5-ethylpyridine in procedures referred to above to produce 2-bromo-5-ethylpyridine, which is then reacted with copper, under heating conditions, to produce 5,5'-diethyl-2,2'-bipyridine).

E. 4,7-Diethyl-1,10-Phenanthroline 4,7-Diethyl-1,10-phenanthroline may be prepared as follows:

A stirred mixture of 1 molar proportion of o-nitroaniline, 1 mole of arsenic acid hemihydrate, 4 moles of sulfuric acid in 96.8% solution, and a volume of water equal to ⅓ of the volume of sulfuric acid used is heated to 100° C. and treated with 2 moles of 1-chloro-3-pentanone (available from Aldrich Chemical Co., Inc.) at such a rate that the temperature does not exceed 140° C. Heating is continued at this temperature for 2 hours. The mixture is then poured into water, made alkaline, and the precipitate removed by filtration. Both the filtrate and the precipitate are extracted with hot benzene. After removal of the solvent, the resulting 4-ethyl-8-nitroquinoline is crystallized from benzene-petroleum ether.

An alternative procedure for preparing 4-ethyl-8-nitroquinoline is as follows:

A stirred mixture of 1 molar proportion of o-nitroaniline, 2 moles of arsenic acid hemihydrate and 85% phosphoric acid (100 ml per 0.1 mole of o-nitroaniline) is heated to 100° C. and 1-chloro-3-pentanone (1.3 moles) is added dropwise at such a rate that the temperature does not exceed 105° C. This temperature is maintained for an additional 0.5 hours. The reaction mixture is then poured onto ice and neutralized with concentrated ammonium hydroxide. The resulting precipitate and filtrate are extracted with hot benzene, and the combined extracts are evaporated to dryness. The resulting 4-ethyl-8-nitroquinoline is recrystallized from benzene-petroleum ether.

4-Ethyl-8-nitroquinoline is reduced to 4-ethyl-8-aminoquinoline by catalytic reduction with Adams' catalyst as follows: place a solution of 0.05 moles of 4-ethyl-8-nitroquinoline in 100 ml of rectified spirit (ethyl alcohol) together with 0.1 g of Adams' catalyst (platinum (IV) oxide, available from Aldrich Chemical Co., Inc.) in a hydrogenation flask, and shake in hydrogen. After the theoretical volume of hydrogen is absorbed, filter off the platinum with suction and rinse the reaction vessel with rectified spirits. Evaporate the alcohol from the combined filtrate and washings on a water bath. Dissolve the crude residue in rectified spirits, add a little decolorizing charcoal, boil and filter. Heat the filtrate to boiling, add hot water to initiate crystallization and allow to cool.

The same procedures specified above for making 4-ethyl-8-nitroquinoline may now be used for making 4,7-diethyl-1,10-phenanthroline by substituting 4-ethyl-8-aminoquinoline for o-nitroaniline.

F. 5,6-Diethyl-1,10-Phenanthroline 5,6-Diethyl-1,10-phenanthroline may be made by the following procedure:

A mixture of 175 ml of fuming nitric acid (specific gravity of 1.59–1.60) and 87.5 ml of glacial acetic acid is cooled to 10° C. While this solution is stirred vigorously, 50 g of o-diethylbenzene is added at a rate to maintain the temperature between 10°–20° C. After the last of the o-diethylbenzene is added, the stirring is continued for 45 minutes at the same temperature. The reaction mixture is then poured into 1 liter of ice water. The crude nitro compound is extracted with 4×125 ml portions of ether and the ether extract is washed with 3×50 ml portions of water, with 6×50 ml portions (until the reaction becomes alkaline) of 10% sodium hydroxide solution and again with 3×50 ml portions of water. The ether extract is then dried over anhydrous sodium sulfate, and the solvent removed. Product is distilled from a Claisen flask at 10 mm Hg pressure. The fraction boiling at 130°–150° C. is collected. The column used is 60 centimeters long, 1.5 centimeters internal diameter and filled with small, single-turn glass helices. The fractionating head is designed so that any desired portion of the condensate can be returned to the column. The material is fractionated three consecutive times into three degree ranges between 120°–141° C. 1,2-Diethyl-4-nitrobenzene is collected in the boiling range 139°–141° C. at 10 mm Hg pressure.

1,2-Diethyl-4-nitrobenzene is then converted to 3,4-diethylaniline by the following procedure: 1,2-diethyl-4-nitrobenzene is reduced catalytically in a Parr hydrogenator at initial pressures of 60 pounds per square inch (p.s.i.), using platinum oxide, platinum on zirconium or palladium on zirconium oxide. 17.9 g (0.1 moles) of 1,2-diethyl-4-nitrobenzene is dissolved in 150 ml of absolute alcohol and 0.2 g of platinum oxide is added. At 24° C. the reduction is 97% complete in 20 minutes and 100% in 1 hour. The catalyst and solvent are removed and the 3,4-diethylaniline is distilled at 10 mm Hg pressure to yield product.

Next, 3,4-diethylaniline is converted to 4,5-diethyl-2-nitrocarbethoxyanilide by the following procedure:

28.7 g (0.193 moles) of 3,4-diethylaniline, 73-ml of acetone, 43 ml of water and 34 ml of sodium hydroxide solution (24%) and 29 g of ethylchlorocarbonate are used to prepare the urethan. The urethan is used directly in the nitration, which is accomplished in a mixture of 118 ml of concentrated nitric acid and 43 ml of concentrated sulfuric acid. After the product is poured onto ice and solidifies, it is dissolved in ether. The ether solution is washed with water until neutral, dried over anhydrous sodium sulfate, and the solvent is removed on a steam-bath. Product is recrystallized from alcohol.

Next, 4,5-diethyl-2-nitrocarbethoxyanilide is converted to 4,5-diethyl-2-nitroaniline by the following procedure:

To a solution of 20 g of sodium hydroxide, 50 ml of water and 150 ml of alcohol, 12.1 g (0.062 moles) of 4,5-diethyl-2-nitrocarbethoxyanilide is added. While the solution is stirring, the temperature is raised to 70° C. and held there for one hour. The alcohol is removed under diminished pressure and 100 ml of water added. The suspension is extracted repeatedly with benzene. The benzene solution is dried over anhydrous sodium sulfate and the benzene removed under diminished pressure. The residue is recrystallized from dilute alcohol. The nitroaniline product is steam distillable. The nitroaniline product is isolated by steam distillation and the distillate is extracted with ether. After the ether extract is dried and the ether is removed, the residue is distilled at reduced pressure to produce 4,5-diethyl-2-nitroaniline.

5,6-Diethyl-8-nitroquinoline may be produced by the above alternative procedures for making 4-ethyl-8-nitroquinoline from o-nitroaniline by substituting 3.5 moles of glycerol for the 2 moles of 1-chloro-3-pentanone in the procedure which uses sulfuric acid.

5,6-Diethyl-8-nitroquinoline is converted to 5,6-diethyl-8-aminoquinoline by treatment with Adams' catalyst as described above. 5,6-Diethyl-8-aminoquinoline is then converted to 5,6-diethyl-1,10-phenanthroline by the same procedure as described above for converting 4,5-diethyl-2-nitroaniline to 5,6-diethyl-8-nitroquinoline, except that heating upon glycerol addition is continued for 25 minutes rather than 2 hours. 5,6-Diethyl-1,10-phenanthroline is recrystallized from petroleum ether.

G. 5,6-Diphenyl-1,10-Phenanthroline 5,6-Diphenyl-1,10-phenanthroline can be produced by the same procedure that produces 5,6-diethyl-1,10-phenanthroline, except in the first reaction in the sequence that ultimately forms the phenanthroline product, o-diphenylbenzene is used as starting material rather than o-diethylbenzene.

II. Synthesis of Os(R)(R')Z$_2$

A. Os(R)(R')Cl$_2$

Os(R)(R')Cl$_2$ may be made by the following procedure:

19.335 g K$_2$OsCl$_6$ (0.04019 moles) and 0.08512 moles of R+R' (for example, if R and R' are both 2,2'-bipyridine, a total of 13.295 g 2,2'-bipyridine is 0.08512 moles) are dissolved in about 400 ml N,N'-dimethylformamide (DMF). The resulting solution is stirred and heated to reflux, which is maintained for 1 hour (avoid overboiling).

Following reflux, reaction vessel contents are cooled to 30°–40° C. over a period of 1–2 hours. The resulting mixture is vacuum filtered using a medium grade fritted glass filter. The reaction vessel is rinsed with 20 ml DMF and the rinse is filtered over the fritted filter. The resulting filtrate is transferred to a 3 liter (l) beaker and stirred.

To the stirring solution, a solution of 22.799 g Na$_2$S$_2$O$_4$ in 2 l deionized water is added dropwise over 45 minutes. The resulting mixture is cooled in an ice bath for more than 3 hours. The cooled mixture is then filtered under vacuum using Whatman qualitative filter paper in a ceramic filter. The filtered solids are then washed twice with 50 ml water, twice with 50 ml methanol, and twice with 50 ml ether. The filtered solid product is dried under high vacuum (approximately 30 inches Hg at 50° C. for more than 15 hours (or overnight)). Product is transferred to a brown bottle with a screw-on cap, and the bottle is stored in a desiccator at room temperature.

B. Os(R)(R')Br$_2$

The above procedure may be modified to make Os(R)(R')Br$_2$ by substituting the 0.04019 moles of K$_2$OsCl$_6$ for an equivalent molar amount of (NH$_4$)$_2$OsBr$_6$, available from Strem or Johnson Matthey. (K$_2$OsCl$_6$ is available from Strem, Aldrich or Johnson Matthey.)

The synthetic procedures described above may be used to make the Os(R)(R')Z$_2$ compounds referred to above. However, reaction conditions and product isolation procedures in some cases may need to be adjusted in a way that is well within the ordinary skill level in the art of synthetic chemistry.

III. Synthesis of [Os(II)(R)(R')imZ]Y

A. [Os(II)(R)(R')imZ]Cl

The synthesis of [Os(II)(R)(R')imZ]Cl is given immediately below:

0.0244 moles Os(R)(R')Cl$_2$ and 2.30 g imidazole (0.0338 moles) are dissolved in 1200 ml of 50:50 (volume:volume) ethanol:deionized water. These contents are stirred and heated to reflux, which is maintained for 6 hours (avoid overboiling). After reflux, stirring is continued and the reaction mixture is cooled to 30°–40° C. over a period of one hour. Next, solvent is rotary evaporated. The resulting residue (product) is rinsed with 50 ml ether. Product is then dried under high vacuum (approximately 30 inches Hg) at 50° C. for more than 15 hours (overnight). After drying, product is transferred to a brown bottle having a screw-on cap and stored in a desiccator at room temperature.

B. [Os(II)(R)(R')imZ]Br

The compound [Os(II)(R)(R')imZ]Br may be produced rather than [Os(II)(R)(R')imZ]Cl by substituting 0.0243 moles of Os(R)(R')Br$_2$ for 0.0244 moles of Os(R)(R')Cl$_2$ in the above procedure.

C. N-Methylimidazole and N-Ethylimidazole Analogs

The N-methylimidazole and N-ethylimidazole analogs of the above compounds may be made by substituting 0.0338 moles imidazole in the above procedure with 0.0338 moles of N-methylimidazole and N-ethylimidazole, respectively, in the above procedure.

D. Exchange of Counterions

At this point, the anion (or counterion) of the compound produced is either chloride or bromide. These anions may be substituted with other anions recited in the present application. The osmium mediator compound formed immediately above and having a chloride or bromide counterion, is hydrophilic and soluble in water. To exchange the counterions present in these compounds, first a saturated aqueous solution of the compound should be formed. Next, at least one molar equivalent of ammonium tetrafluoroborate or ammonium perchlorate should be added to the saturated aqueous solution. This procedure will exchange the water soluble compound having a bromide or a chloride counterion with a less water soluble (more organic soluble) compound having a tetrafluoroborate or perchlorate counterion respectively. Now the osmium mediator compound has been converted to an organic soluble compound. The organic soluble compound may be dissolved in acetonitrile. (A saturated solution should be formed.) Now the osmium mediator compound may be converted back to a hydrophilic compound having a chloride, bromide, iodide, flouride, or nitrate counterion by adding at least a molar equivalent of the appropriate tetraethylammonium salt to the saturated acetonitrile solution, thereby precipitating the now hydrophilic osmium mediator compound having a chloride, bromide, iodide, flouride, or nitrate, counterion.

E. Alternate Method for Synthesis of [Os(II)(R)(R')imZ]Y

An alternative procedure for the synthesis of [Os(II)(R)(R')imZ]Y, wherein im can be imidazolyl, N-methylimidazolyl, or N-ethylimidazolyl, may be illustrated by the following synthesis of [Os(II)(bpy)$_2$imCl]BF$_4$:

5.00 g (8.72 mmol) Os(bpy)$_2$Cl$_2$ and 0.819 g imidazole were dissolved in 315 ml mixture (2:1,volume:volume) of ethanol and deionized water. The solution was heated to reflux and refluxed for six hours. Next, the resulting solution was cooled to room temperature, and ethanol was removed by rotary evaporation. Upon addition of 1.377 g (13.13 millimoles (mmol)) NH$_4$BF$_4$, precipitate formed. After the mixture was cooled in an ice bath for thirty minutes, the precipitate was collected by filtration and washed with 20 ml deionized water and 20 ml ether. Finally, the product, [Os(II)(bpy)$_2$imCl]BF$_4$, was dried under vacuum at 50° C.

[Os(II)(bpy)$_2$imBr]BF$_4$ may be synthesized by substituting an equimolar amount of Os(bpy)$_2$Br$_2$ for Os(bpy)$_2$Cl$_2$ in the procedure immediately above.

Counterions may be exchanged by the procedure under Section III.D. above, entitled Exchange of Counterions.

IV. Synthesis of [Os(III)(R)(R')imZ]$^{+2}$XY$_n$

A. [Os(III)(R)(R')imZ]$^{+2}$BF$_4$Y; [Os(III)(R)(R')imZ]$^{+2}$SO$_4$; and [Os(III)(R)(R')imZ]$^{+2}$ClY 9.50 millimoles (mmol) [Os(II)(R)(R')imZ]Y is dissolved in 2·1 CH$_3$CN and stirred under N$_2$ atmosphere. Next, 1.136 g NOBF$_4$ (9.73 mmol) is added to the solution and stirring under N$_2$ atmosphere is continued for 45 minutes at room temperature. An additional 0.6666 g NOBF$_4$ (5.71 mmol) is added to the resulting solution and stirring under N$_2$ atmosphere is continued for 2 hours at room temperature. Next, solvent is rotary evaporated and the resulting residue (product) is rinsed with 100 ml ether. Product, [Os(III)(R)(R')imZ]$^{+2}$BF$_4$Y, is then dried under high vacuum (approximately 30 inches Hg) at 50° C. for more than 72 hours (over the weekend). Finally, product is transferred to a brown bottle with a screw-on cap and stored in a desiccator at room temperature.

Oxidizing agents which can be used instead of nitrosonium tetrafluoroborate include nitrosonium sulfate, and nitrosonium chloride.

B. Exchange of Counterions

A partial or complete exchange of counterions for [Os(III)(R)(R')imZ]$^{+2}$XY$_n$ may be accomplished by the scheme described in III.D. above (that is, by converting the compounds from hydrophilic to hydrophobic or hydrophobic to hydrophilic and precipitating by the appropriate combination of solvents and salts described in III.D.). Additionally included in the list of tetraethylammonium salts that form hydrophilic compounds are tetraethylammonium sulfate, tetraethylammonium carbonate, and tetraethylammonium sulfite.

To form [Os(III)(R)(R')imZ]$^{+2}$SO$_4$, [Os(III)(R)(R')imZ]$^+$$_2$CO$_3$, or [Os(III)(R)(R')imZ]$^{+2}$SO$_3$, an organic soluble compound, such as [Os(III)(R)(R')imZ]$^{+2}$(BF$_4$)$_2$, could be dissolved in a sufficient amount of acetonitrile to form a saturated solution. Next, tetraethylammonium sulfate, tetraethylammonium carbonate, or tetraethylammonium sulfite is added to the saturated solution to precipitate the respective sulfate, carbonate, or sulfite salt.

C. Alternate Oxidation Methods

An alternative method for oxidizing [Os(II)(R)(R')imZ]Y to [Os(III)(R)(R')imZ]$^{+2}$XY$_n$ is to dissolve [Os(II)(R)(R')imZ]Y in an appropriate solvent (for example, water, if the compound has a counterion, as stated above, which makes the compound hydrophilic, or acetonitrile, if the compound has a perchlorate or tetrafluoroborate counterion), and then add an appropriate acid to lower the pH below 3. Next, oxygen is bubbled into the solution and the Os(II) mediator compound is oxidized to Os(III) mediator compound. A wide range of acids could be used in this procedure (for example, hydrochloric acid, hydrobromic acid, hydriodic acid, hydrofluoric acid, perchloric acid, nitric acid, or sulfuric acid).

Another alternative method for oxidizing [Os(II)(R)(R')imZ]Y to [Os(III)(R)(R')imZ]$^{+2}$XY$_n$ is exemplified below with the conversion of [Os(II)(bpy)$_2$imCl]BF$_4$ to [Os(III)(bpy)$_2$imCl]Cl$_2$.

[Os(II)(bpy)$_2$imCl]BF$_4$, wherein im is imidazolyl, was converted to [Os(III)(bpy)$_2$imCl]Cl$_2$ as follows: 4.50 g (6.49 mmol) of [Os(II)(bpy)$_2$imCl]BF$_4$ was dissolved in 180 ml acetonitrile. Next, 0.912 g (7.81 mmol) NOBF$_4$ was added and the reaction was allowed to proceed at room temperature for 45 minutes. Next, 2.688 g (16.22 mmol) of tetraethylammonium chloride was added slowly to the stirring solution. Product was precipitated by pouring reaction contents onto 240 ml acetone with rapid stirring. After the resulting mixture was cooled in dry ice for 15 minutes, precipitate was collected by filtration and washed twice with 50 ml acetone. Finally, the product was dried under vacuum at 50° C.

This second alternative oxidation method should be applicable to other [Os(II)(R)(R')imZ]Y compounds. Counterions may be exchanged by the procedures described above.

As stated above, the compounds of the present invention may be used as redox mediators in electrochemical biosensors, such as the biosensor described in Pollmann et al. (referred to above). Because such biosensors measure analytes from biological fluid, which is aqueous based, highly aqueous soluble redox mediators are greatly preferred. Redox mediators of the present invention have at least about 1 millimolar aqueous solubility, but the solubility of these mediators in a particular application may need to be much greater than 1 millimolar. For example, when measuring the concentration of glucose (in a blood or serum sample) with the device described in Pollmann et al., redox mediator concentration in the reagent (before drying of the reagent) should be at least about 150 millimolar (mM) and is preferably at least about 160 mM.

Choice of counterion (anion) for the compounds of the present invention greatly influence aqueous solubility of the compounds (the more hydrophilic the counterion, the more aqueous soluble the redox mediator). The arrow drawn below shows counterions of increasing hydrophilicity (from left to right). Compounds of the present invention with counterions on the right hand side of the arrow will be more aqueous soluble than compounds with counterions on the left hand side of the arrow. Compounds with a PF$_6$— counterion are poorly soluble and are not part of the present invention.

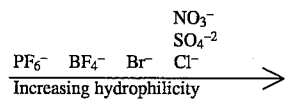

To illustrate the low oxidation potential of the compounds of the present invention, cyclic voltammetry of [Os(III)(bpy)$_2$imCl]Cl$_2$, wherein im is imidazolyl, was conducted as follows (see FIG. 1): [Os(III)(bpy)$_2$imCl]Cl$_2$ was dissolved in 0.1 N Na$_2$SO$_4$ solution. Sufficient [Os(III)(bpy)$_2$imCl]Cl$_2$ was dissolved in 0.1 N Na$_2$SO$_4$ solution to provide a solution that was 1.89 millimolar (mM) in [Os(III)(bpy)$_2$imCl]Cl$_2$. Next, a gold circular disk working electrode (diameter=2 millimeters (mm)), a platinum mesh counter electrode (a platinum wire grid) and a silver/silver chloride reference electrode were immersed into this solution and a cyclic voltammagram was taken by scanning the potential between −0.2 volts and 0.6 volts. A typical voltammagram is shown in FIG. 1. The voltammagram shows that this Os(III) redox mediator is part of a highly reversible redox couple. Typical results for the voltammagram shown in FIG. 1 are as follows (results normalized by molar concentration):

|  | Anodic | Cathodic |  |
|---|---|---|---|
| Peak Potential | 0.150 ± 0.01 | 0.095 ± 0.01 | Volt vs Silver/Silver Chloride |
| Peak Current | 1.90 ± 0.1 | 2.30 ± 0.1 | milliamps (mA)/molar (M) |

A very similar voltammagram resulted from cyclic voltammetry of [Os(III)(bpy)$_2$imCl]Cl$_2$, wherein im is N-methylimidazolyl. Under the same conditions as described above, this N-methylimidazolyl analog showed a reversible redox couple, an oxidation peak at +0.14 volts vs. silver/silver chloride (anodic peak potential), and a reduction peak at +0.08 volts vs. silver/silver chloride (cathodic peak potential). (FIG. 2) (μA in FIGS. 1 and 2 means microamps).

As stated above, oxidation of osmium, by oxygen, in the present inventive compounds is slow. For example, [Os(II)(bpy)$_2$imCl]Cl, wherein im is imidazolyl, can be converted to [Os(III)(bpy)$_2$imCl]Cl$_2$ by dissolving [Os(II)(bpy)$_2$imCl]Cl in 30 millimolar HCl and bubbling oxygen gas into the resulting solution for about 19 hours. However, when the pH is above 3, an aqueous solution of [Os(II)(bpy)$_2$imZ]Y is stable.

The fast reaction kinetics between the electroactive center of an enzyme and the compounds of the present invention may be illustrated by FIG. 5. In a glucose assay that utilizes a reagent of the present invention that includes glucose oxidase in a biosensor, such as the biosensor described in Pollmann et al., the reaction involving glucose, glucose oxidase and osmium (III)-containing redox mediator competes with the reaction involving glucose, glucose oxidase, and oxygen. The later reaction will result in an error in the glucose assay because it does not lead to generation of current that my be correlated to the concentration of glucose in the sample being measured. The faster the reaction kinetics of the former reaction, as compared to the later reaction, then the less significant is the error due to the later reaction.

Therefore, in an assay that has very little or insignificant interference from the reaction with oxygen described above, the assay result should be virtually identical between a sample of venous blood (with low oxygen content) and a sample of oxygenated blood (with high oxygen content), wherein each sample contains an equivalent concentration of glucose. FIG. 5 shows a comparison of dose response curves for venous and oxygenated whole blood samples.

Figure 5A:
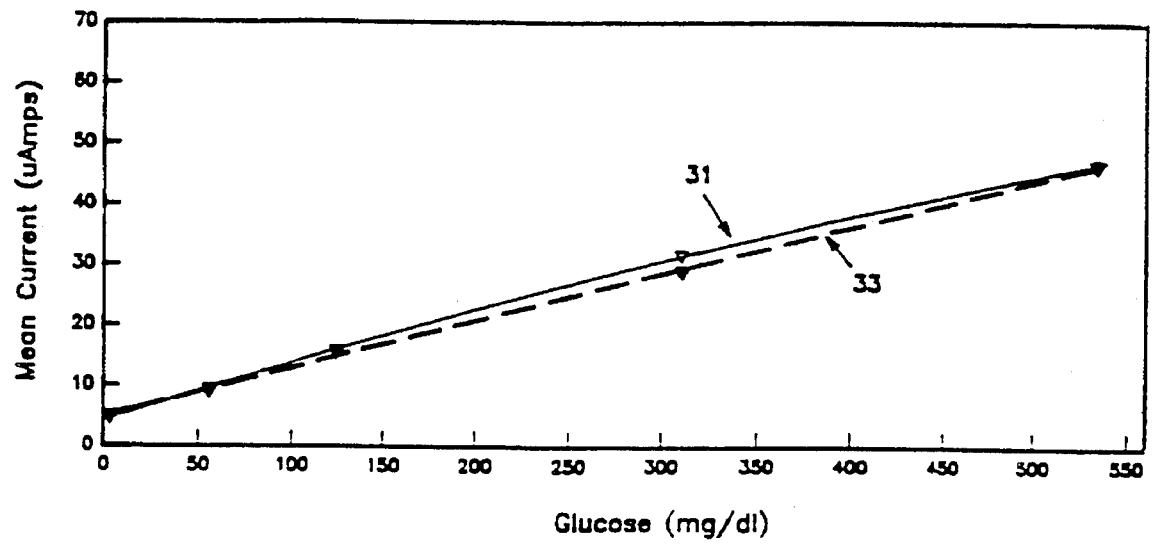
FIG. 5a illustrates fast reaction kinetics between the electroactive center of glucose oxidase and one of the compounds of the present invention.

FIG. 5a) shows a comparison of a glucose assay for a sample of venous blood 31 and a glucose assay for a sample of oxygenated whole blood 33. The reagent utilized for these assays was prepared similarly to Reagent Example 1 below, but included the following components in the following concentrations (before reagent drying): 300 millimolar (mM) 3-sulfobenzoic acid, 0.07% (by weight) Triton X-100 surfactant, 160 mM [Os(III)(bpy)$_2$imCl]$^{+2}$Cl$_2$, wherein im is N-methylimidazolyl, and 3000 tetramethylbenzidine (TMB) units glucose oxidase per milliliter reagent, and the pH of the reagent was adjusted to 4.25. Six microliters of this reagent were added to reagent well 9 of the biosensor described in Pollmann et al., and then dried for 6 minutes at about 50° C. A venous or oxygenated whole blood sample was then added to reagent well 9 and the resulting test sample was incubated at room temperature for 20 seconds. Next, the palladium working and counter electrodes were separated by +150 millivolts (mV). Ten seconds after this potential difference was applied, current was measured and correlated to the concentration of glucose in the sample.

Figure 5B:
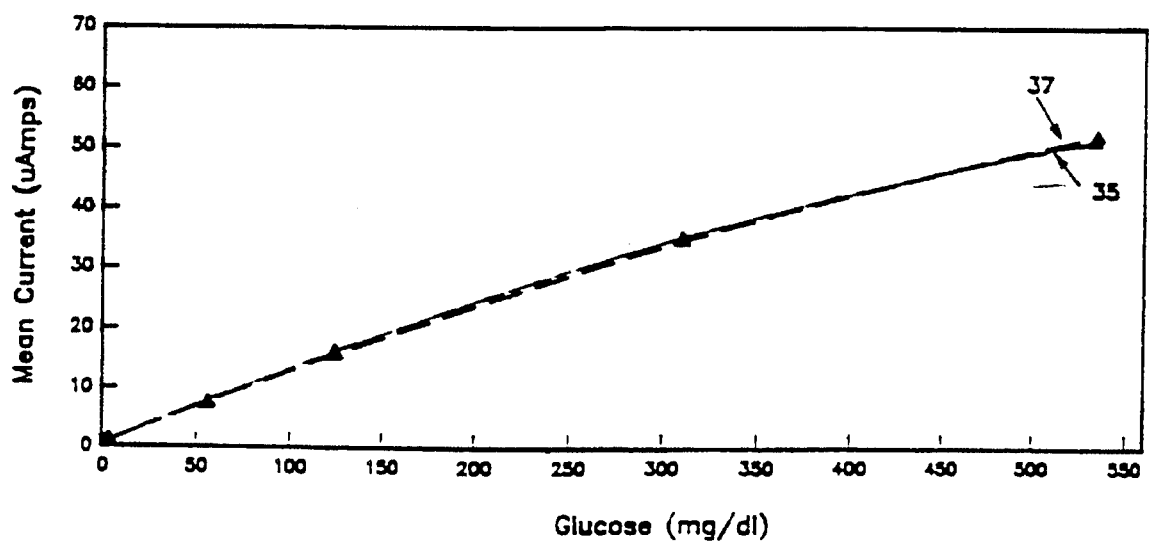
FIG. 5b illustrates fast reaction kinetics between the electroactive center of glucose oxidase and another compound of the present invention.

FIG. 5b) shows another comparison of a glucose assay for a sample of venous whole blood 35 and oxygenated whole blood 37. The apparatus and assay method were as described for FIG. 5a). The reagent had the following components in the following amounts (before reagent drying): 150 mM 3-sulfobenzoic acid, 150 mM $[Os(III)(bpy)_2imCl]Cl_2$, wherein im is imidazolyl, 3000 TMB units glucose oxidase per ml reagent, 100 mM $MgCl_2$, 0.09% (by weight) Igepal CO-530 surfactant (available from Rhone-Poulenc), and a reagent pH of 5.5.

Figure 5C:
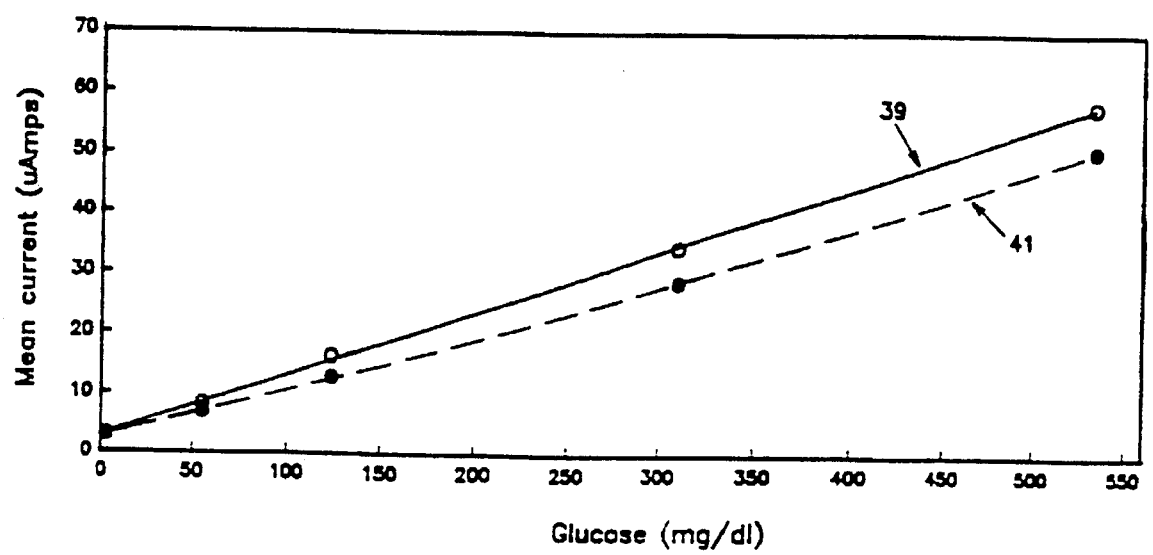
FIG. 5c illustrates the reaction kinetics between the electroactive center of glucose oxidase and potassium ferricyanide.

FIG. 5c) shows still another comparison of a glucose assay for a sample of venous whole blood 39 and oxygenated whole blood 41. For these assays, the apparatus was the same as for FIGS. 5a) and 5b), but the reagent was formulated by the procedure for formulating a glucose reagent described in Pollmann et al., but with the following components in the following amounts (before drying the reagent): 250 mM potassium phosphate buffer, about 14 grams microcrystalline cellulose per liter of reagent, 300 mM potassium ferricyanide, 0.5 grams Triton X-100 surfactant per liter of reagent, 1.6 million TMB units glucose oxidase per liter of reagent, 0.6 grams hydroxyethylcellulose per liter of reagent, and 37 mM disodium succinate (disodium succinate was used rather than potassium glutamate in the formulation disclosed in Pollmann et al.), and a reagent pH of 6.6. The assay method was as described for FIGS. 5a) and 5b), except that the working and counter electrodes were separated by +300 mV rather than +150 mV.

FIGS. 5a) and 5b), which included two different redox mediators of the present invention show very little assay error due to the oxygen reaction, while FIG. 5c), which uses ferricyanide as a mediator, shows substantially more assay error due to competition from the oxygen reaction, thereby implying that the reaction kinetics are faster between the electroactive center of glucose oxidase and $[Os(III)(bpy)_2imCl]Cl_2$, wherein im is imidazolyl or N-methylimidazolyl, than between the electroactive center of glucose oxidase and ferricyanide.

Figure 2:
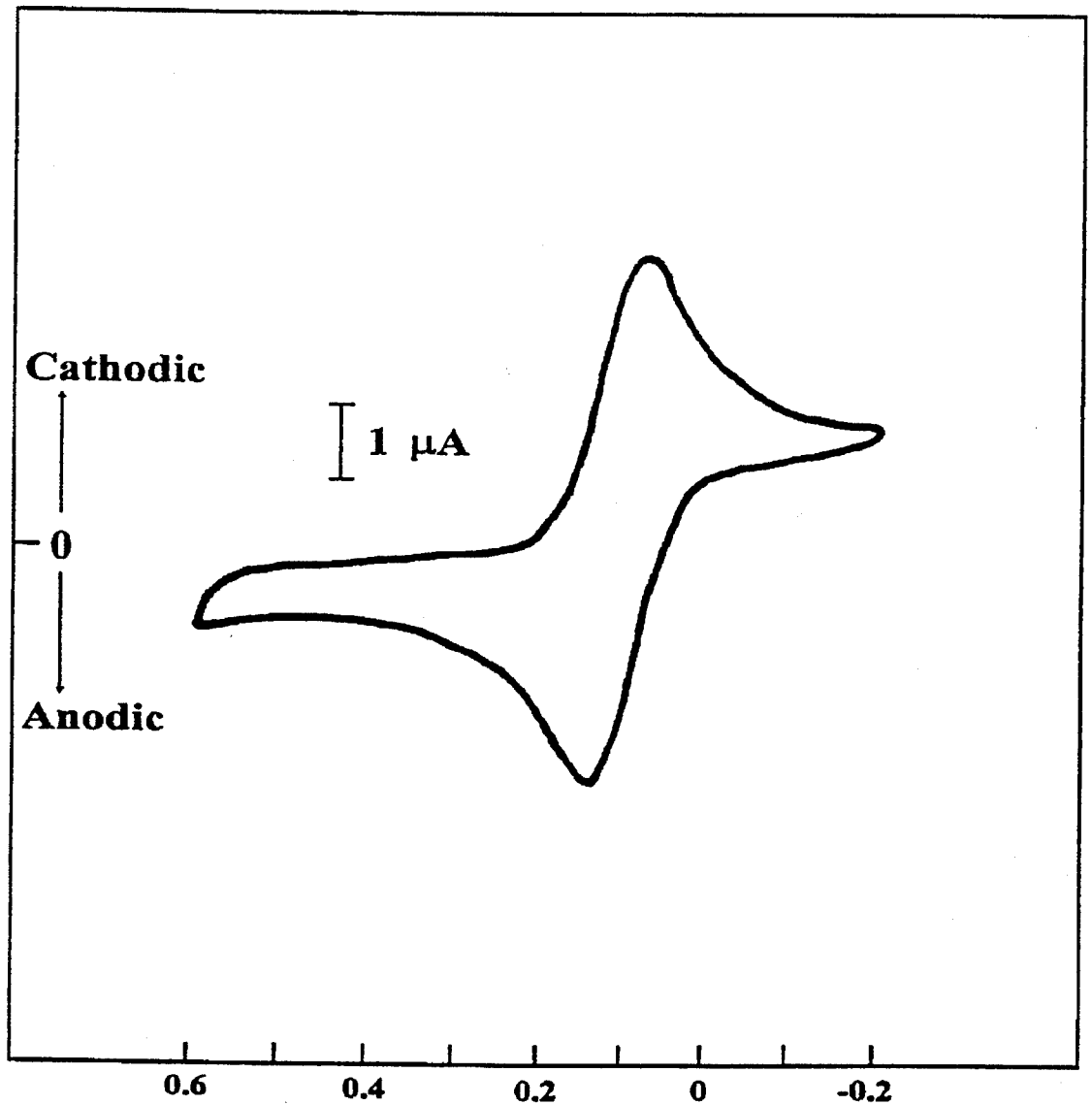
FIG. 2 is a cyclic voltammagram of [Os(III)(bpy)$_2$imCl]Cl$_2$, wherein im is N-methylimidazolyl.

Assays performed with eletrochemical biosensors that utilize a redox mediator, which is oxidized or reduced at the electrode surface to produce a current that correlates to the concentration of analyte being measured, are subject to error if other substances, which do not correlate to the concentration of analyte being measured, in the sample are oxidized or reduced and contribute to the current measured. Because the redox mediators of the present invention have low oxidation potentials (FIGS. 1 and 2 show mediators with oxidation potentials of 0.15 volts (vs. Ag/AgCl) and 0.14 volts (vs. Ag/AgCl), respectively), assays performed with these redox mediators may be conducted at low applied potentials. The use of low applied potentials should oxidize fewer interfering sample substances, such as bilirubin, acetaminophen, ascorbic acid and uric acid in blood samples.

When utilized as a redox mediator in an electrochemical biosensor, the compounds of the present invention may be incorporated into a reagent that is used in the biosensor to measure analytes from a fluid sample, such as a blood sample. Such reagent formulations are exemplified below by Reagent Example No. 1 and Reagent Example No. 2, which may be utilized as a reagent for measuring glucose in the biosensor described in Pollmann et al.

REAGENT EXAMPLE NO. 1

A reagent for measuring glucose from a blood sample was formulated as follows: A 160 millimolar (mM) solution of $[Os(III)(bpy)_2imCl]^{+2}Cl_2$, wherein im is imidazolyl, in 150 mM 3-sulfobenzoic acid (pH 5.50) that also included 0.06% (by weight) Triton X-100 surfactant and glucose oxidase at a concentration of 3,000 TMB units/milliliter reagent. (Triton surfactants are comprised of various polyoxyethylene ethers and other surface-active compounds. Triton surfactants are available from Sigma Chemical Company. Triton is a registered trademark of Rohm and Haas Co.) Six microliters (μl) of this reagent may be added to reagent well 9 of the biosensor described in Pollmann et al., dried for 6 minutes at about 50° C., and then used to measure the amount of glucose in the blood sample. For example, as described in Pollmann et al., a blood sample may be added to the reagent well, the enzymatic reaction is allowed to go to completion, and then the working and counter electrodes may be separated by a potential difference of about 150 millivolts (mV). After this potential difference has been applied, current may be measured (for example, at 7 and ½ seconds after the potential has been applied to the working and counter electrodes) and may be correlated to glucose concentration of the blood sample.

REAGENT EXAMPLE NO. 2

The reagent in this example is formulated similarly to the reagent of Example 1, except 100 mM potassium phosphate buffer (pH 6.80) is used rather than 150 mM 3-sulfobenzoic acid (pH 5.50). An assay for glucose may be conducted in the same manner as described above in Reagent Example No. 1.

In the reagents recited above (Reagent Examples No. 1 and No. 2), it is preferred to have from about 25 mM to about 200 mM amounts (before reagent drying) of a reagent stabilizer that is magnesium chloride, magnesium sulfate, zinc sulfate, manganese sulfate, or nickel chloride. (25 mM magnesium chloride is particularly preferred.)

The redox mediator in the above reagents should be in a concentration (before reagent drying) of at least about 150 mM and is preferably in a concentration of at least about 160 mM. The concentration of 3-sulfobenzoic acid is preferably in a concentration range from about 100 mM to about 300 mM (300 mM is particularly preferred), and the pH of a reagent that includes 3-sulfobenzoic acid is preferably from about 4.25 to about 5.5. (A pH of 4.5 is particularly preferred.)

Phosphate buffer, or other buffer provided in the above reagents, is preferably in a concentration range from about 100 mM to about 200 mM (before reagent drying).

Preferred surfactants in the above reagents are Triton X-100 surfactant (available from Sigma Chemical Company) and IGEPAL CO-610 surfactant (nonylphenoxypoly (ethylenoxy) ethanol, branched, available from Phone-Poulenc), preferably in a concentration from about 0.01% (by weight) to about 0.1% (by weight), and most preferably at a concentration of about 0.06% (by weight).

Film formers, such as UCAR® Vehicle 451 film former (a water dilutable styrene-acrylic latex that includes about 42% (by weight) polymer plus proprietary additives, about 58% (by weight) water, and about 0.03% (by weight) formaldehyde, available from Union Carbide) or ELVACE film former (a vinyl acetate copolymer, available from Reichhold Chemicals, Inc., product No. 40709-00) may be included in the reagent in a preferred concentration from about 3% to about 6% (by weight) (3% by weight is most preferred). (All of the above concentrations are reagent concentrations before drying of the reagent in reagent well 9 described in Pollmann et al.)

Figure 6A:
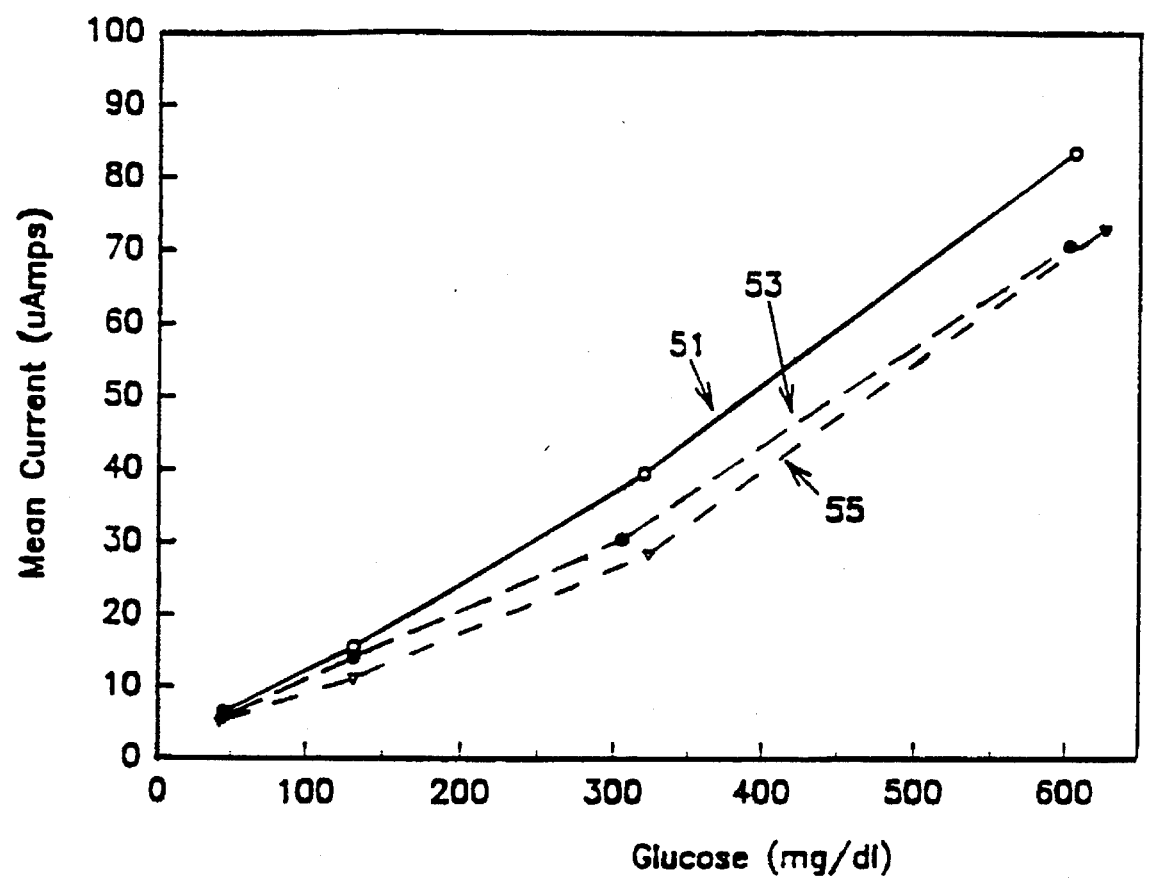
FIG. 6a shows hematocrit effect in a glucose assay performed with potassium ferricyanide.

A particular advantage that has been discovered with [Os(III)(bpy)$_2$imCl]Cl$_2$, wherein im is imidazolyl, for a glucose assay performed by the electrochemical biosensor described in Pollmann et al. is a reduced hematocrit effect when glucose is measured from a whole blood sample. FIG. 6a) shows dose response curves for measuring glucose from a whole blood sample that has a 19% hematocrit (51), a 45% hematocrit (53), and a 75% hematocrit (55). (The assay was performed with the biosensor strip, reagent, and method described for FIG. 5c), except test sample incubation time was 35 seconds rather than 20 seconds. This reagent utilized a ferricyanide mediator.)

Figure 6B:
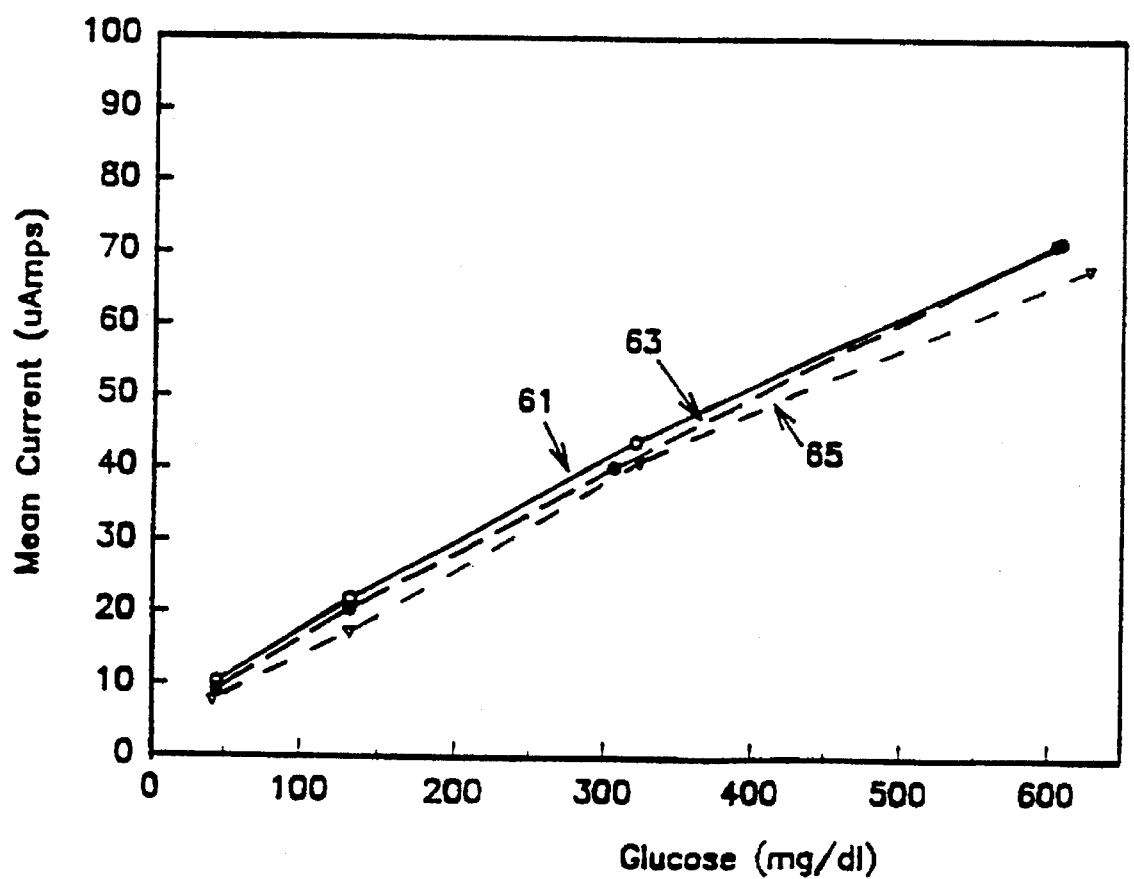
FIG. 6b shows reduced hematocrit effect in a glucose assay performed with one of the compounds of the present invention.

FIG. 6b) shows results of an identically conducted assay, except the reagent utilized was formulated similarly to Reagent Example No. 1, described above, and included the following components in the following amounts (before reagent drying): 150 mM 3-sulfobenzoic acid, 0.06% (by weight) Triton X-100 surfactant, 125 mM [Os(III)(bpy)$_2$imCl]Cl$_2$, wherein im is imidazolyl, 3000 TMB units glucose oxidase per ml reagent, and a reagent pH of 5.5.

In FIG. 6b), 61 represents the sample with 19% hematocrit, 63 represents the sample with 45% hematocrit, and 65 represents the sample with 75% hematocrit.

The dose response curves in FIG. 6b) are closer together than the dose response curves in FIG. 6a), thereby indicating that a glucose assay performed with a particular mediator of the present invention, [Os(III)(bpy)$_2$imCl]Cl$_2$, wherein im is imidazolyl, is influenced less by the hematocrit level of the sample than a glucose assay performed with ferricyanide, a common redox mediator used in such assays.

REAGENT EXAMPLE NO. 3

First a polymer matrix was formed by mixing a composition that is 100 mM 2-(N-morpholino) ethanesulfonic acid (MES buffer), 0.02% (by weight) Triton X-100 surfactant, 1% (by weight) polyvinyl alcohol (10,000 molecular weight, 88% hydrolyzed). The pH of this mixture was adjusted to 6.55, thereby forming the polymer matrix.

Next, 6,000 units of glucose oxidase and 4.5 milligrams (7.0 micro moles) of [Os(II)(bpy)$_2$imCl]Cl, wherein im is imidazolyl, were added to 1 milliliter of the polymer matrix described above. One microliter (μl) was added to the working electrode of each of the five biosensor systems described below and the reagent was dried for 15 minutes at 45° C. After drying, glucose was measured from a blood sample or a 20 mM phosphate buffered saline solution.

The electrochemical biosensors utilized with Reagent Example No. 3 (above) and Reagent Example No. 4 (below) are different than the biosensor described in Pollmann et al.. The biosensor systems used to conduct assays with Reagents 3 and 4 are described immediately below.

BIOSENSOR SYSTEMS FOR REAGENT EXAMPLES NOS. 3 AND 4

Biosensor System No. 1 (a three electrode system)

The working electrode was comprised of a sputtered gold film on a silica wafer base. This electrode was 2 millimeters (mm)×2 mm square.

Figure 3:
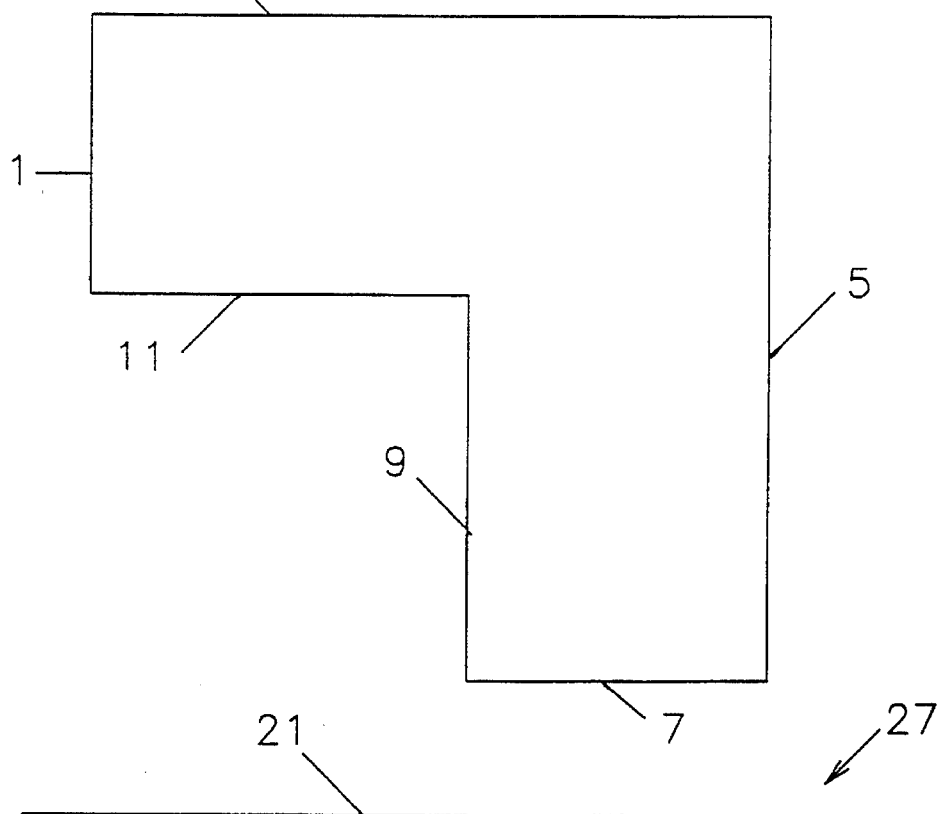
FIG. 3 shows the configuration of a counter electrode of a biosensor system that may be used with the present invention.

The counter electrode was also comprised of a sputtered gold film on a silica wafer base and its dimensions are shown in FIG. 3. In FIG. 3, side 1 is 2 mm, side 3 is 3.5 mm, side 5 is 5 mm, side 7 is 2 mm, side 9 is 3 mm, and side 11 is 1.5 mm.

The reference electrode was comprised of a sputtered silver film on a silica wafer base. The film's surface was treated with ferric chloride in dilute acid to form a silver chloride surface layer. The reference electrode dimensions were similar to the dimensions of the counter electrode.

Biosensor System No. 2 (a three electrode system)

Working electrode 25 (FIG. 4) was constructed similarly to the working electrode of Biosensor System No. 1. Working electrode dimensions were 1 mm×1 mm square.

Figure 4:
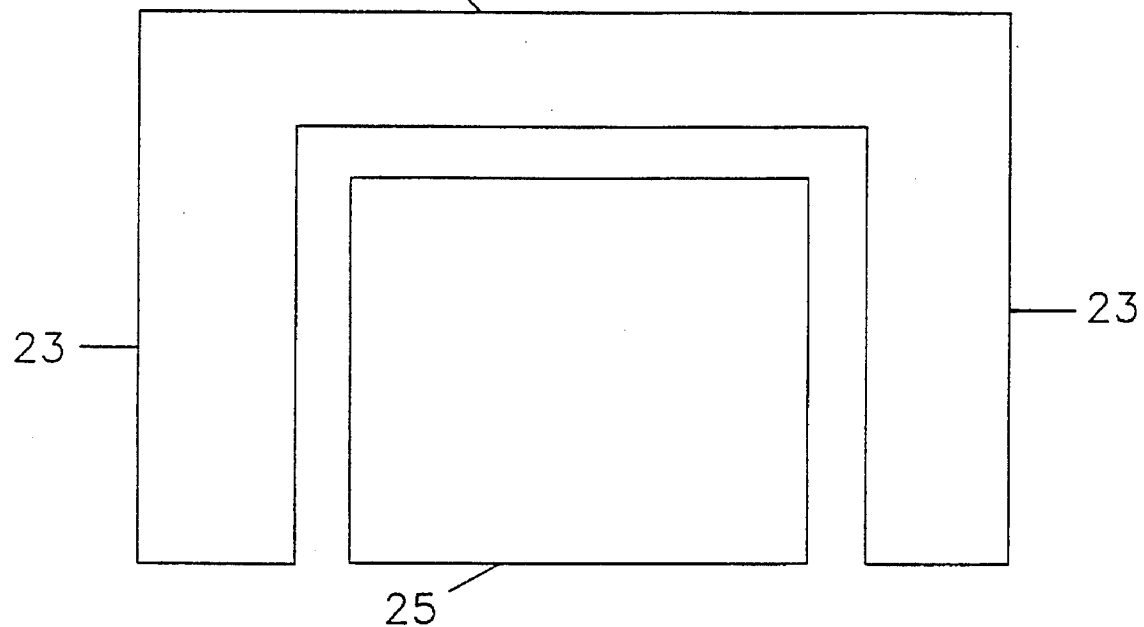
FIG. 4 shows the configuration of working and counter electrodes of a biosensor system that may be used with the present invention.

Counter electrode 27 was a sputtered gold film on a silica wafer and shaped as shown in FIG. 4. In FIG. 4, side 21 is 1.6 mm in length and sides 23 are 1.3 mm in length. Counter electrode 27 was dimensioned so that the working electrode could be positioned as shown in FIG. 4.

The reference electrode was an external silver/silver chloride electrode.

Biosensor System No. 3 (a two electrode system)

The working electrode was constructed similarly to the working electrode of Biosensor System No. 2.

The reference electrode was a sputtered silver film treated in the same fashion as the reference electrode in Biosensor System No. 1 to form a silver chloride surface layer. The reference electrode was dimensioned the same as the counter electrode in Biosensor System No. 2 and the working and reference electrodes were positioned with respect to each other in the same fashion as the working and counter electrodes of Biosensor System No. 2.

Biosensor System No. 4 (a two electrode system)

The working electrode was comprised of sputtered gold film on 10 mil FR4 fiberglass circuit board. Electrode dimensions were defined by a photoimageable solder resist (Enplate DSR-3242 from Enthone-Omi, a negative resist). Electrode dimensions were 1 mm×1 mm square.

The reference electrode was comprised of sputtered silver film on FR4 fiberglass. The electrode surface was painted with a screen printable silver/silver chloride ink (Acheson Colloids DB 2268) to make a silver/silver chloride reference electrode. The surface area of the reference electrode was defined by insertion of a 10 mil plastic spacer, which had a U-shaped cutout portion at one end and an adhesive on opposing sides. The space was positioned between the working and reference electrodes, thereby defining a capillary space between the working and reference electrodes. This electrode system includes a sample introduction port and a vent hole in the working and/or reference electrode so that a fluid sample may be added to the capillary space.

The construction of this electrode system is more fully described in FIGS. 1–6 and in the discussion of FIGS. 1–6 of the Specification in co-pending, commonly owned by Boehringer Mannheim Corporation, U.S. patent application of Kordal et al., entitled "A Method Of Fabricating Electrodes For Use In A New Electrochemical Sensor", Ser. No. 180,499, filed on even date herewith, the disclosure of which is hereby incorporated by reference.

Biosensor System No. 5 (a two electrode system)

The working electrode was comprised of sputtered gold film on 7 mil polyester, sold under the mark Mylar. The working electrode was circular (a 1.5 mm diameter circle) and was defined by a screen printed pattern using screen printable UV curable dielectric ink (for example, Acheson Colloids ML 25198) or a heat curable dielectric ink (for example, Metech 7192M).

The reference electrode was constructed in the same fashion as described above for Biosensor System No. 4, and the arrangement of working and reference electrodes, separated by a spacer, was as described above for Biosensor System No. 4.

Measuring Glucose

As described above, 1 μl of the reagent described in Reagent Example No. 3 was applied to the working electrode of each of the 5 Biosensor Systems described immediately above and dried at 45° C. for 15 minutes.

To measure glucose from a blood or 20 mM phosphate buffered saline sample, the potential of the working electrode may be poised at 150 mV vs. the silver/silver chloride reference electrode to oxidize [Os(II)(bpy)$_2$imCl]Cl in situ (after application of the blood sample or buffered saline sample) to [Os(III)(bpy)$_2$imCl]Cl$_2$ at the working electrode surface. After the blood or buffered saline sample is added to the electrode system, [Os(III)(bpy)$_2$imCl]Cl$_2$, which is generated in situ as described above, is reduced to [Os(II)(bpy)$_2$imCl]Cl by the reaction involving glucose, glucose oxidase, and [Os(III)(bpy)$_2$imCl]Cl$_2$. [Os(II)(bpy)$_2$imCl]Cl is then re-oxidized to [Os(III)(bpy)$_2$imCl]Cl$_2$ at the working electrode surface, thereby generating a current, which may be correlated to the concentration of glucose in the blood or buffered saline sample.

REAGENT EXAMPLE NO. 4

First, a buffer polymer matrix is formed by mixing together a composition that is 150 mM N-2-hydroxyethylpiperazine-N'-2-ethanesulfonic acid (HEPES buffer) 20 mM magnesium sulfate, 1% (weight:weight) polyvinyl alcohol (10,000 molecular weight, 88% hydrolyzed), and 15 mM adenosine triphosphate(ATP). This composition is adjusted to pH 8.00, thereby forming the buffer polymer matrix.

To 1 milliliter of the buffer polymer matrix is added 3 milligrams (mg) (4.7 micromoles) [Os(II)(bpy)$_2$imCl]Cl, wherein im is imidazolyl, 1,333 units glycerol-3-phosphate oxidase, and 3,333 units glycerol kinase. Approximately 1.5 microliters of the resulting reagent may be added to the working electrode of Biosensor System No. 1, described above, and dried at 45° C. for 15 minutes.

Glycerol may be measured from a glycerol-containing fluid sample in a manner analogous to the measurement of glucose with Reagent Example No. 3.

Poising the potential of the working electrode at 150 mV vs. silver/silver chloride will oxidize [Os(II)(bpy)$_2$imCl]Cl in situ (after application of the glycerol-containing fluid sample) to [Os(III)(bpy)$_2$imCl]Cl$_2$ at the surface of the working electrode. After the glycerol-containing fluid sample is added to the electrode system, glycerol and ATP react in the presence of glycerol kinase and magnesium sulfate to form L-α-glycerol-3-phosphate and adenosine diphosphate. L-α-glycerol-3-phosphate is then involved in a reaction with glycerol phosphate oxidase and [Os(III)(bpy)$_2$imCl]Cl$_2$, thereby converting L-α-glycerol-3-phosphate to dihydroxyacetone phosphate and [Os(III)(bpy)$_2$imCl]Cl$_2$ to [Os(II)(bpy)$_2$imCl]Cl. [Os(II)(bpy)$_2$imCl]Cl is re-oxidized to [Os(III)(bpy)$_2$imCl]Cl$_2$ at the working electrode surface, thereby generating a current that may be correlated to the concentration of glycerol in the sample.

The compounds of the present invention may be used as redox mediators to measure other analytes described in Pollmann et al. Further, although inclusion of a buffer is preferred in the reagents specified above, it is not required. Also, improvements in the power source and meter described in Pollmann et al. are described in U.S. Pat. No. 4,963,814 (issued Oct. 16, 1990), U.S. Pat. No. 4,999,632 (issued Mar. 12, 1991), U.S. Pat. No. 4,999,582 (issued Mar. 12, 1991), and U.S. Pat. No. 5,243,516 (issued Sep. 7, 1993), the disclosures of which are hereby incorporated by reference.

The present invention has been disclosed in the above teachings and drawings with sufficient clarity and conciseness to enable one skilled in the art the make and use the invention, to know the best mode for carrying out the invention, and to distinguish it from other inventions and from what is old. Many inventions and obvious adaptations of the invention will readily come to mind, and these are intended to be contained within the scope of the invention as claimed below.

We claim:

1. A compound having the formula:

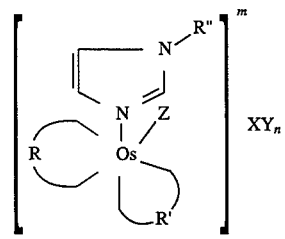

wherein

R and R' are the same or different and are 2,2'-bipyridyl, 4,4'-disubstituted-2,2'-bipyridyl, 5,5'-disubstituted-2,2'-bipyridyl, 1,10-phenanthrolinyl, 4,7-disubstituted-1,10-phenanthrolinyl, or 5,6-disubstituted-1,10-phenanthrolinyl, wherein the disubstitution is a methyl, ethyl, or phenyl group, R and R' are coordinated to Os at their nitrogen atoms, R" is hydrogen, methyl or ethyl, Z is chloro or bromo, m is +1 or +2, X is an anion and is chloride, bromide, iodide, fluoride, tetrafluoroborate, perchlorate, nitrate, sulfate, carbonate, or sulfite, Y is an anion and is chloride, bromide, iodide, fluoride, tetrafluoroborate, perchlorate or nitrate, and n is 1 or zero, but when X is sulfate, carbonate, or sulfite, n is zero, and when m is 1, n is zero and X is not sulfate, carbonate or sulfite, wherein the aqueous solubility of the compound is greater than about 1 millimolar.

2. The compound of claim 1, wherein R and R' are the same or different and are 2,2'-bipyridyl, 4,4'-disubstituted-2,2'-bipyridyl, or 5,5'-disubstituted 2,2'-bipyridyl, wherein the disubstitution may be a methyl, ethyl, or phenyl group.

3. The compound of claim 2, wherein R" is hydrogen or methyl.

4. The compound of claim 3, wherein Z is chloro.

5. The compound of claim 4, wherein

X is an anion and is chloride, bromide, or tetrafluoroborate,

Y is an anion and is chloride, bromide, or tetrafluoroborate, and when m is 2, n is 1 and when m is 1, n is zero.

6. The compound of claim 1, wherein R and R' are 2,2'-bipyridyl.

7. The compound of claim 6, wherein R" is hydrogen or methyl.

8. The compound of claim 7, wherein Z is chloro.

9. The compound of claim 8, wherein

X is an anion and is chloride, bromide, or tetrafluoroborate,

Y is an anion and is chloride, bromide, or tetrafluoroborate, and when m is 2, n is 1 and when m is 1, n is zero.

10. The compound of claim 9, wherein

R" is hydrogen,

X is an anion and is chloride or tetrafluoroborate,

Y is an anion and is chloride or tetrafluoroborate, and when m is 2, n is 1 and when m is 1, n is zero.

11. A compound having the formula:

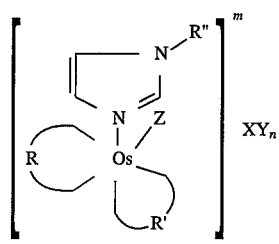

wherein

R and R' are the same or different and are 2,2'-bipyridyl, 4,4'-dimethyl-2,2'-bipyridyl, 4,4'-diphenyl-2,2'-bipyridyl, 1,10-phenanthrolinyl, 4,7-dimethyl-1,10-phenanthrolinyl, 4,7-diphenyl-1,10-phenanthrolinyl, or 5,6-dimethyl-1,10-phenanthrolinyl, R and R' are coordinated to Os at their nitrogen atoms, R" is hydrogen, methyl or ethyl, Z is chloro or bromo, m is +1 or +2, X is an anion and is chloride, bromide, iodide, fluoride, tetrafluoroborate, perchlorate, nitrate, sulfate, carbonate, or sulfite, Y is an anion and is chloride, bromide, iodide, fluoride, tetrafluoroborate, perchlorate or nitrate, and n is 1 or zero, but when X is sulfate, carbonate, or sulfite, n is zero, and when m is 1, n is zero and X is not sulfate, carbonate or sulfite, wherein the aqueous solubility of the compound is greater than about 1 millimolar.

* * * * *